US012127861B2

(12) United States Patent
Baker et al.

(10) Patent No.: US 12,127,861 B2
(45) Date of Patent: Oct. 29, 2024

(54) SYSTEMS AND METHODS FOR PACKAGING INSTRUMENTS

(71) Applicant: RST Automation LLC, Bronx, NY (US)

(72) Inventors: Russell Baker, Sunnyside, NY (US); Lawrence Zelner, New York, NY (US)

(73) Assignee: RST AUTOMATION, LLC, Bronx, NY (US)

( * ) Notice: Subject to any disclaimer, the term of this patent is extended or adjusted under 35 U.S.C. 154(b) by 83 days.

(21) Appl. No.: 15/068,420

(22) Filed: Mar. 11, 2016

(65) Prior Publication Data

US 2016/0264275 A1   Sep. 15, 2016

Related U.S. Application Data

(60) Provisional application No. 62/132,212, filed on Mar. 12, 2015.

(51) Int. Cl.
  *A61B 50/30* (2016.01)
  *A61L 2/00* (2006.01)
  *A61L 2/28* (2006.01)

(52) U.S. Cl.
  CPC ............... *A61B 50/30* (2016.02); *A61L 2/00* (2013.01); *A61L 2/28* (2013.01); *A61B 2050/314* (2016.02); *B65B 2210/04* (2013.01)

(58) Field of Classification Search
  CPC ..... A61B 50/30; A61B 2050/314; A61L 2/00; B65B 2210/04; B65B 57/00; B65B 61/02
  USPC ......... 53/415, 411, 459, 474, 168, 155, 170, 53/263, 238; 700/216, 225, 235
  See application file for complete search history.

(56) References Cited

U.S. PATENT DOCUMENTS

| 4,943,939 | A | 7/1990 | Hoover |
| 5,105,600 | A | 4/1992 | DePoint, Jr. |
| 6,195,967 | B1* | 3/2001 | Todd ................... B65B 1/02 53/562 |
| 7,752,085 | B2 | 7/2010 | Monroe |
| 8,438,817 | B2* | 5/2013 | Sankaran ............ B65B 5/045 53/411 |
| 8,562,274 | B2* | 10/2013 | Murray ............... B65B 39/02 414/222.02 |
| 9,272,796 | B1* | 3/2016 | Chudy ................. B65B 5/10 53/58 |
| 2011/0005342 | A1* | 1/2011 | Treat .................... A61L 2/22 73/865.8 |

FOREIGN PATENT DOCUMENTS

WO   WO 2009/076452   6/2009

OTHER PUBLICATIONS

EP 16762679.5 Extended Search Report.

* cited by examiner

*Primary Examiner* — Hemant Desai
*Assistant Examiner* — Mary C Hibbert-Copeland
(74) *Attorney, Agent, or Firm* — ArentFox Schiff LLP

(57) ABSTRACT

Systems and methods for handling and packaging instruments are fully automated thereby eliminating human handling and increasing accuracy of packaging and labeling of the instruments. One system includes an instrument identification element, an element that determines packaging requirements, an element that creates the packaging such as a labeled peel pouch. The system makes the package including the instrument or instruments. The completed packaging is ready of next steps including sterilization.

23 Claims, 5 Drawing Sheets

SYSTEMS AND METHODS FOR PACKAGING INSTRUMENTS

BACKGROUND

When used for medical, surgical and other applications, instruments are generally sterilized prior to use. A common method of preparing instruments for use in sterile environments such as an operating room or medical procedure room is to place a cleaned, but not yet sterilized, instrument into a plastic pouch. The instrument in the pouch is then sterilized in a sterilization device. Typically, instruments are placed in sterilization pouches by human technicians. This involves human handling of the instruments, manual selection of proper pouches, manual labeling of pouches, manual sealing of pouches, and manual logging of data for sterilization records.

Human handling of such instruments prior to sterilization is labor intensive and error prone. It remains desirable to have systems and methods for automating this process.

SUMMARY

The present invention is directed to systems and methods for identifying and packaging instruments and logging production data.

In a first embodiment, a system for packaging instruments includes an input for receiving instrument identification data. The system further includes an instrument processor coupled to the input. The instrument processor includes a database and an instrument analyzer. The database stores instrument type data, instrument packaging data and package labeling data. The instrument analyzer identifies instrument type and determines instrument packaging and labeling using data stored in the database. The instrument analyzer further determines instrument handling, packaging and labeling instructions. An output coupled to the instrument processor sends the handling, packaging and labeling instructions to at least one external device. The at least one external device in various embodiments includes a labeler, a packager and an instrument transfer device.

In one embodiment, the packager is a packaging turret that holds a plurality of sizes or types of instrument pouches. The specific package is selected based on the received instructions from the instrument processor. In an alternative embodiment, the packager is a unit that holds a roll of packaging tubing and cuts and forms a package in response to instructions received from the instrument processor.

The instrument transfer device in a first embodiment is a catch and release mechanism. The instrument transfer device in a second embodiment is a robotic arm. In both these embodiments, the transfer device moves an instrument from a receiving element such as a conveyor or an instrument identification platform and transfers the instrument to a packaging element such as a peel pouch.

The present invention together with the above and other advantages may best be understood from the following detailed description of the embodiments of the invention illustrated in the drawings, wherein:

DRAWINGS

DESCRIPTION

Embodiments of the present invention enable automated processing and packaging and logging of instrument data for a plurality of surgical instruments.

Figure 1:
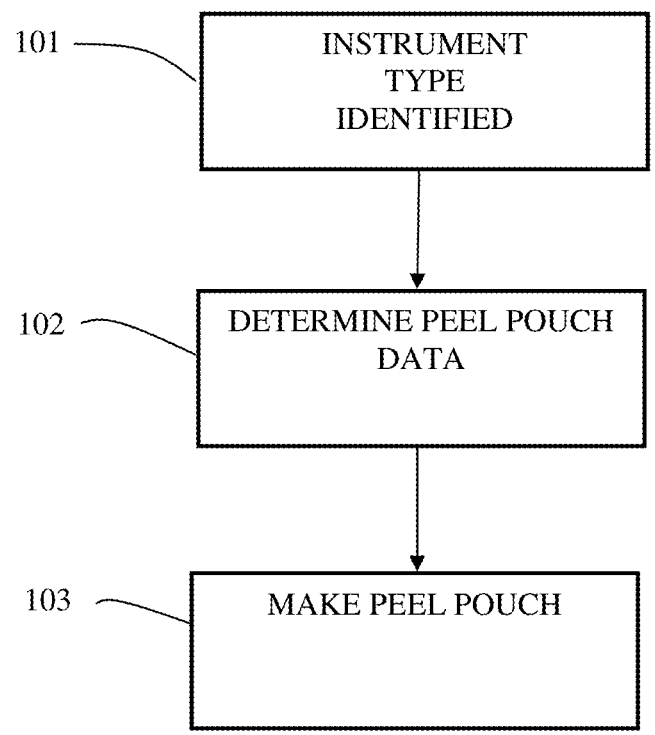
FIG. 1 is a flow chart of the operation of an embodiment of an automated instrument processing and packaging system according to principles of the invention.

A system for automating peel pouch production follows the flow chart in FIG. 1. At step 101, an instrument type is determined. When an instrument enters into the system for processing, the instrument may be labeled or unlabeled. Determining the instrument type may involve reading a label or analyzing the instrument. This is described in greater detail below. At step 102, the data specific to the creation of the peel pouch is determined based on the instrument type. The peel pouch data may include, but is not limited to, the information for the peel pouch label, and the pouch type and size. At step 103, the peel pouch is created, or made. Peel pouch creation includes the steps of producing an appropriately-sized pouch, affixing a label to the pouch, placing one or more instruments inside the pouch, and sealing the pouch.

Figure 2:
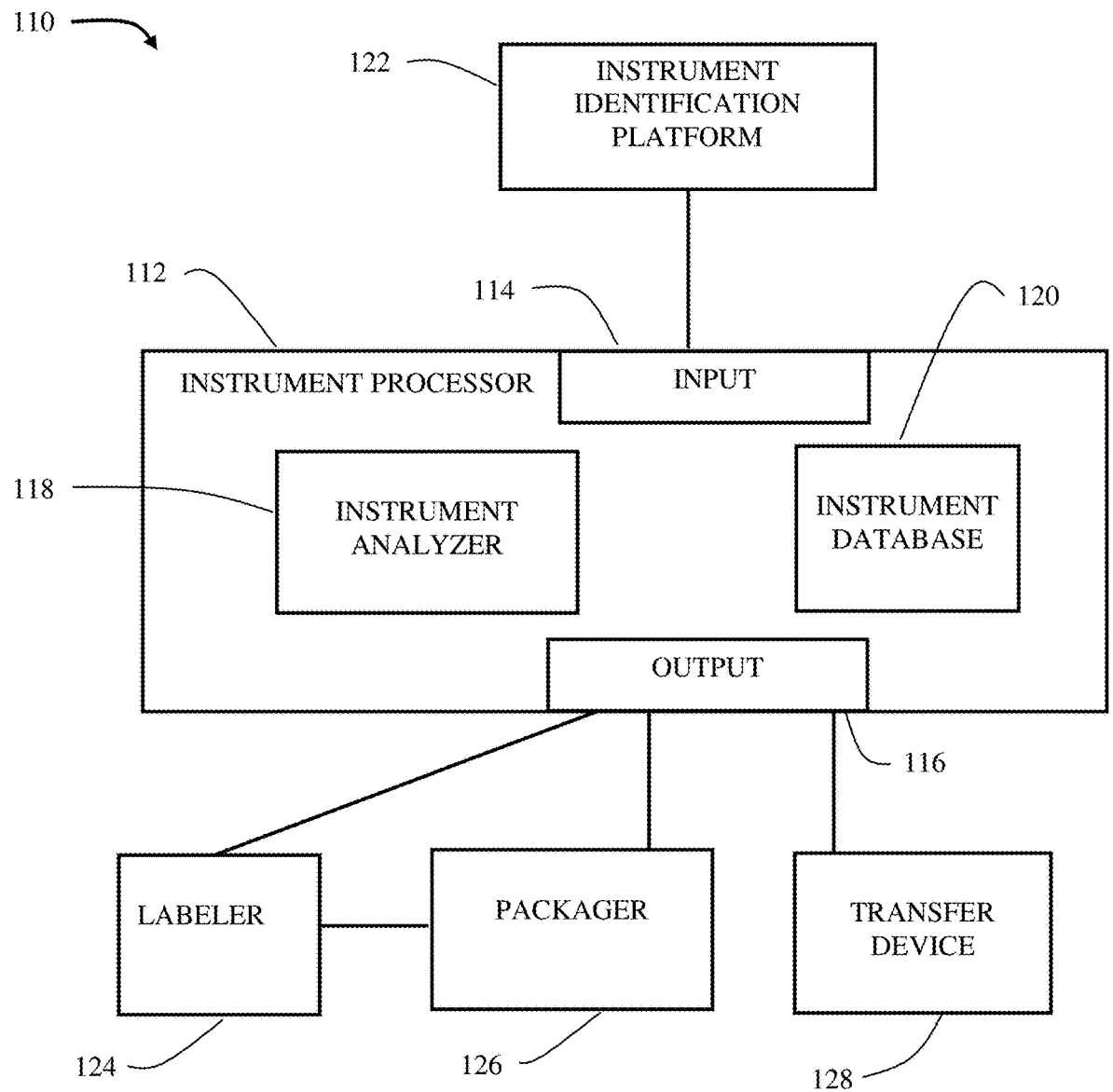
FIG. 2 is a block diagram of an embodiment of an automated instrument processing system according to principles of the invention.

FIG. 2 is a block diagram of an automated instrument packaging system 110. The instrument packaging system 110 includes an instrument processor 112 having an input 114 and an output 116, an instrument analyzer 118 and an instrument database 120. An instrument identification platform 122, a labeler 124, a packager 126 and a transfer device 128 are all in communication with the instrument processor 112.

The instrument identification platform 122 includes one or more instrument identifying devices. The instrument identifying platform 122 automates the process of determining instrument type. One embodiment employs a machine vision system to recognize the instrument type. Another embodiment employs a bar code reader. Yet another embodiment employs an RFID scanner. Other means of recognizing a particular instrument are possible within the scope of the invention. The instrument identification platform submits the instrument identification data to the instrument processor 112 through the input 114.

The instrument analyzer 118 receives the instrument identification data provided by the instrument identification platform 122. If the instrument identification platform was not able to specifically identify the instrument type, the instrument analyzer 118 accesses data stored in the instrument database 120 to identify the particular instrument by comparing the received data with stored data. The instrument analyzer 118 also determines instrument packaging data based on the instrument type and information stored in the instrument database 120.

In one embodiment, the instrument analyzer 118 includes a peel pouch data device. The peel pouch data device receives instrument type information from the instrument identification platform 122 or another source. Using the instrument type, the peel pouch data device may access stored information in the database 120 regarding peel pouch data that pertains to the identified instrument type.

Additional embodiments of the system employ an output device 116. The output device 116 provides data from the peel pouch data device and automates the creation of a peel pouch. One embodiment uses a computer monitor for quickly displaying the peel pouch data and providing instruction to an operator for producing the peel pouch. In an alternative embodiment, the output device is in communication with a labeler 124, for example a printer that produces the label to be affixed to the peel pouch. Additional embodiments include a packager 126, that is, a device for automatically producing a pouch of the required size. The packager 126 may make the pouch from a roll of tubing, or may select a pre-made pouch. In an alternative embodiment of the packager 126, the packager has a selection of pre-made pouches that the packager presents to receive one or more instruments.

In another alternative embodiment, the packager 126 selects a desired amount of packaging material, places the one or more instruments in the selected packaging material, closes and seals the packaging material, prints the label with the selected information and places the label on the package or pouch and sends the instrument data to a log. The log may reside in the packager 126 or alternatively in the instrument database 120. Other locations are possible within the scope of the invention.

The system 110 can include a transfer device 128. In one embodiment, the transfer device 128 is a conveyor to move the one or more instruments both before and after packaging. The transfer device 128 may also include a robotic arm or similar mechanical device to handle the one or more instruments and place them in the selected packaging. In another embodiment, the transfer device 128 may also transfer the package or pouch to a sterilization device.

In one alternative embodiment of the system 110, the labeler 124 prints information directly on the packaging. Alternatively, the label can be affixed to the packaging manually or by an external applicator. In still other embodiments, a sterility indicator may be placed in the selected packaging with the one or more instruments. In other embodiments, the packaging material can be heat sealed after the one or more instruments are placed in it, or it can be sealed by an external means. In still another embodiment, the one or more instruments can be placed in the selected packaging by external means, such as a user, and the system then notified that the packaging is ready to be sealed.

Additionally, the system can be configured to identify and package medical items other than instruments, such as, for example, implantable items and tubing connections.

Figure 3:
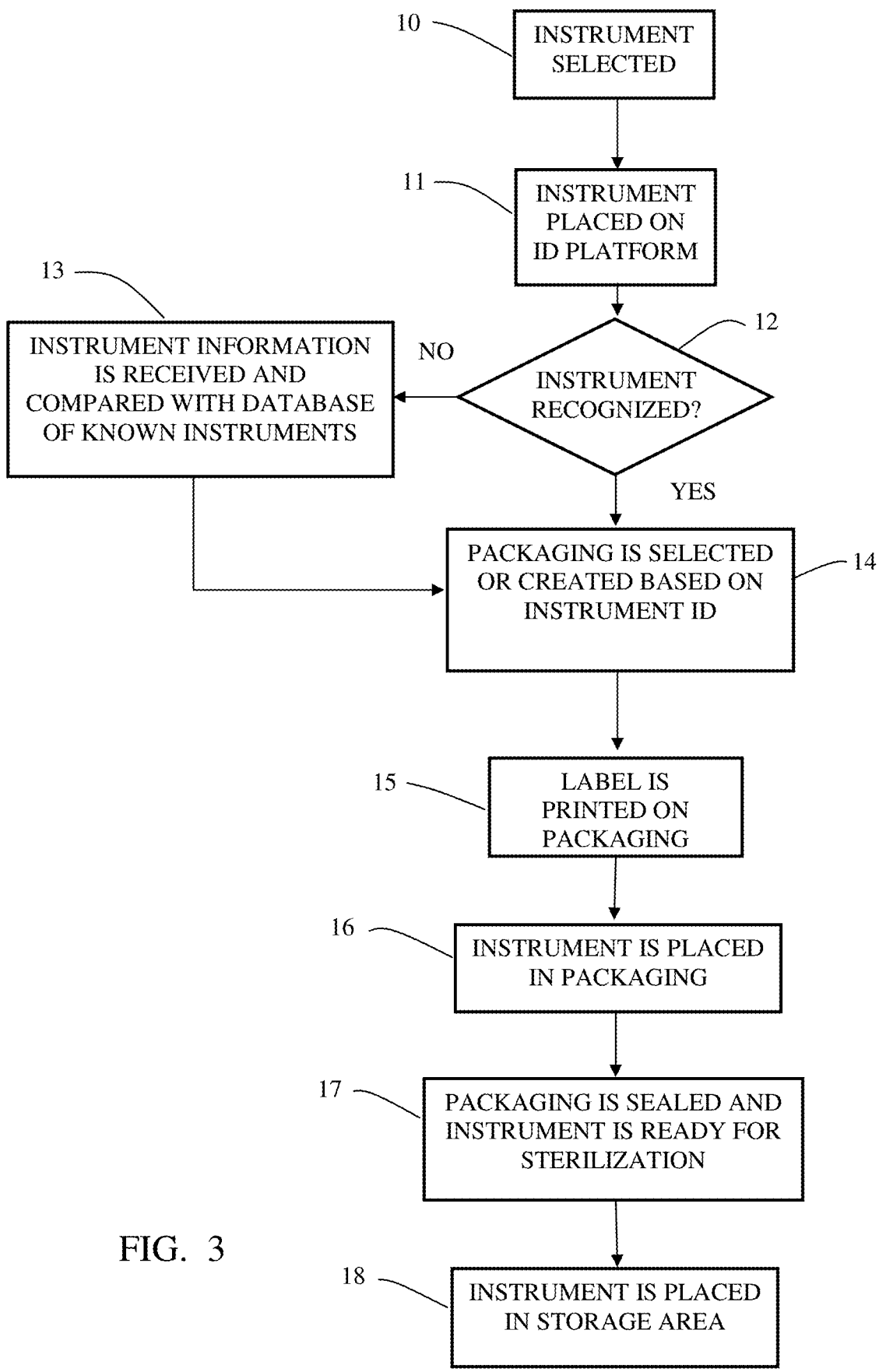
FIG. 3 is a flow chart of the operation of an alternative embodiment of an automated instrument processing and packaging system.

FIG. 3 is a flow chart for the operation of an automated system for the identification, package selection, and packaging of instruments for sterilization such as that shown in the block diagram of FIG. 2. At step 10, the system provides that an instrument is selected. At step 11, the instrument is placed on an instrument identification platform which in one embodiment includes a conveyor. One skilled in the art will recognize that the system may be used for packaging of other components and materials in medical and nonmedical applications.

As shown in FIG. 3, at step 12, the system employs a device to recognize the instrument using, for example, machine vision, barcodes, RFIDs, or other indicia. The recognition device may be incorporated into the system or may be external. If the system recognizes the instrument, the system proceeds to step 14. If the system does not recognize the instrument, the system proceeds to step 13.

At step 13, information about the instrument is compared with a database of known instruments. When the instrument is identified using this comparison, the system proceeds to step 14.

At step 14, the desired packaging is determined and then selected or created based on instrument identification. In a first embodiment, the desired packaging is selected from an inventory of various sizes of packaging. In an alternative embodiment, customized packaging or pouches are cut from bulk packaging material utilizing information from the database of known instruments. The bulk packaging could consist of tubing material.

At step 15, a label is printed on the packaging or alternatively, it is printed on a label which is then applied to the packaging.

At step 16, with continued reference to FIG. 1, the instrument is placed in the desired packaging using mechanical or automated means, including for example, a robotic arm.

At step 17, the packaging is then sealed and the instrument is ready for sterilization.

At step 18, the instrument is then placed in a storage area.

Figure 4:
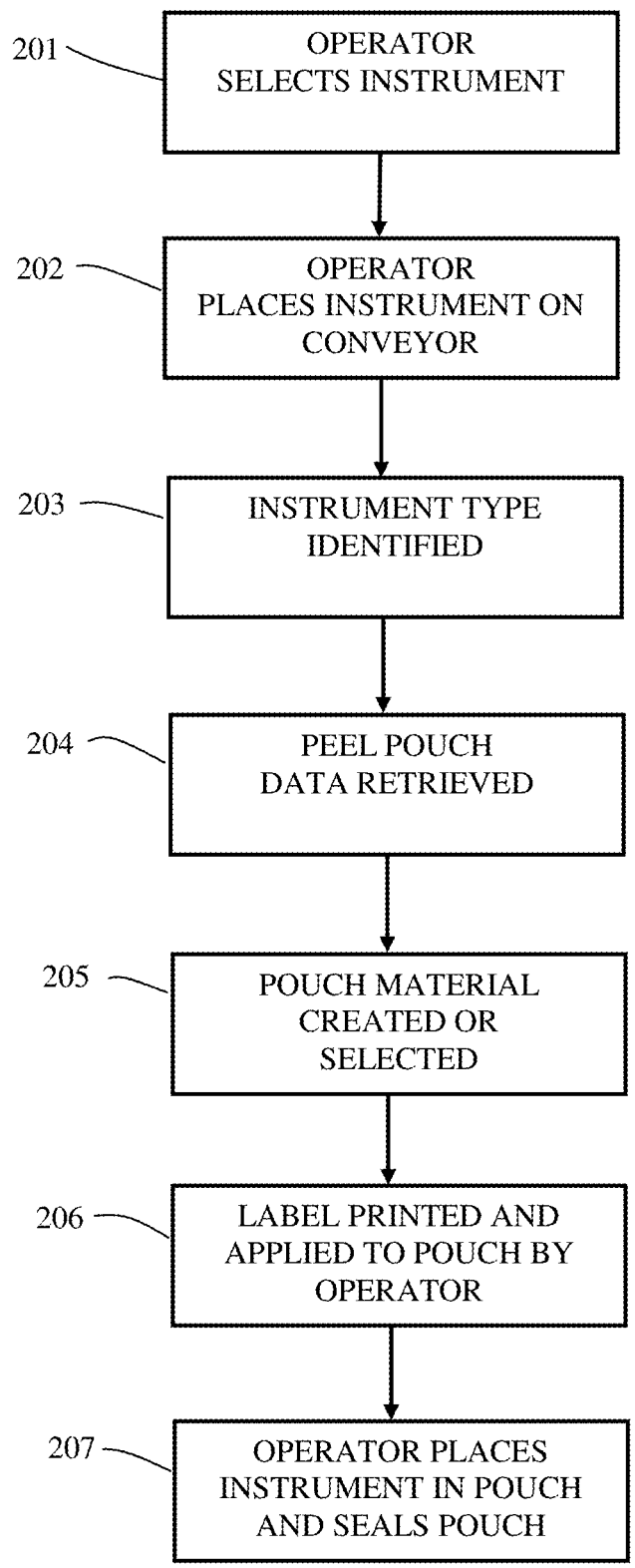
FIG. 4 is a flow chart of the operation of an embodiment of an alternative embodiment of an instrument processing system according to principles of the invention.

FIG. 4 is a flow chart for the operation of another embodiment of an automated system for the identification, package selection, and packaging of instruments for sterilization. At step 201, the system provides that an instrument is selected. At step 202, the instrument is placed on a conveyor and an operator initiates the process. One skilled in the art will recognize that the system may be used for packaging of other components and materials in medical and nonmedical applications.

At step 203, the system employs a device to recognize the instrument using, for example, machine vision, barcodes, RFIDs, or other indicia. The recognition device may be incorporated into the system or may be external.

At step 204, the data related to creating a peel pouch from the identified instrument is retrieved. The data may be stored in a relational database and retrieved by using the instrument type.

At step 205, the desired packaging is created or retrieved. In a first embodiment, the desired packaging is selected from an inventory of various sizes of packaging. In an alternative embodiment, customized packaging or pouches are cut from bulk packaging material utilizing information from the database of known instruments. The bulk packaging could consist of tubing material.

At step 206, a label is printed on the packaging or alternatively, it is printed on a label which is then applied by an operator to the packaging.

At step 207, the operator places the instrument in the pouch and seals it using a heat sealer or equivalent.

Figure 5:
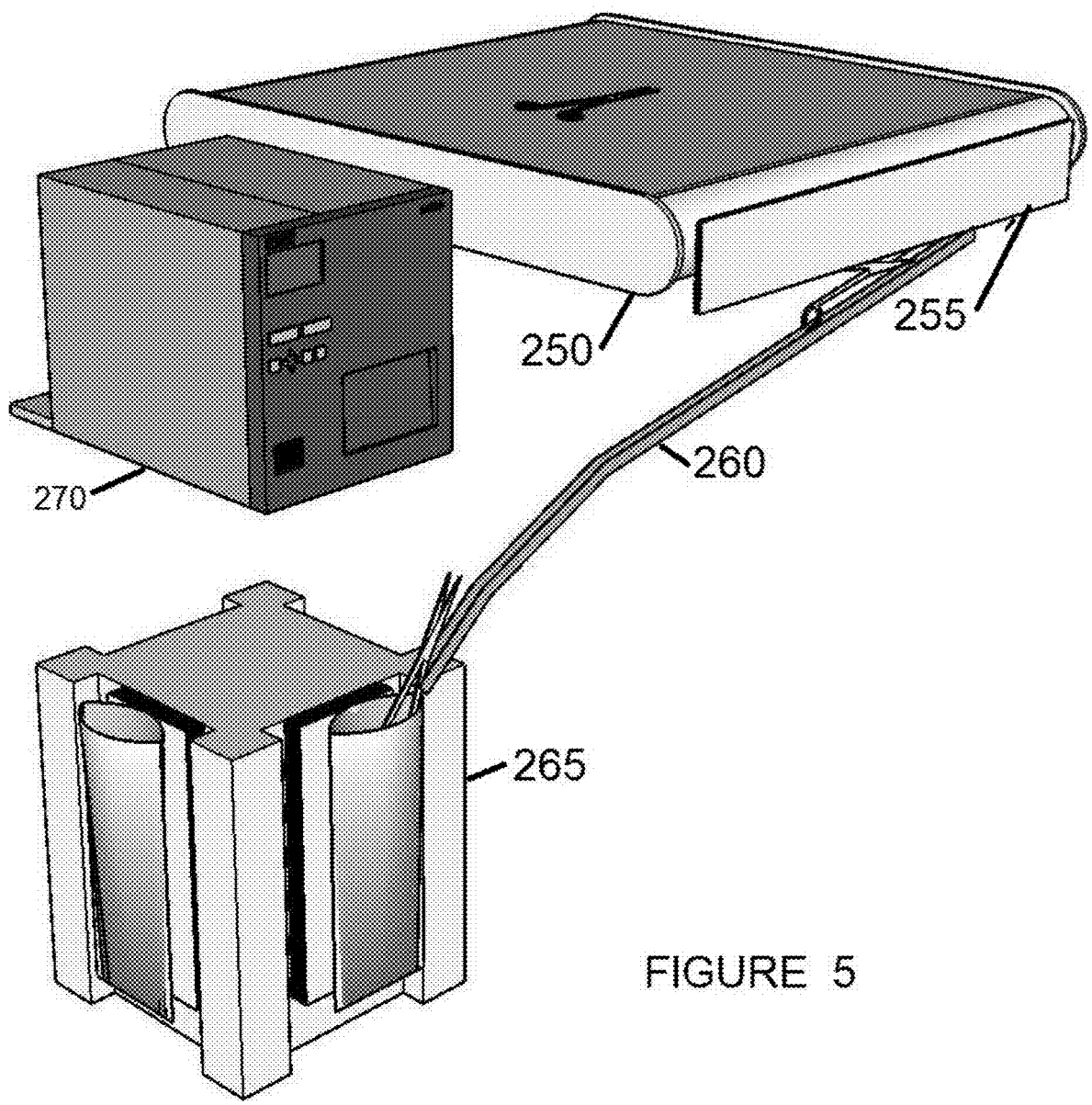
FIG. 5 is an illustration of an alternative embodiment of an automated instrument processing system according to principles of the invention.

FIG. 5 illustrates elements of a system for automated instrument sterilization according to one embodiment of the invention. The system includes a conveyor 250 for instrument conveyance. A catch release mechanism 255 is attached to the conveyor for catching the conveyed instrument. A looped instrument chute 260 is attached to the catch release mechanism and feeds the instrument to a packaging turret 265. The system further includes a label printer 270.

In operation, an instrument to be sterilized is placed on the conveyor. The camera is positioned in relation to the conveyor so that the instrument is in the camera's field of view. The system receives data about the instrument through the camera. In alternative embodiments, other sensors may be used to take instrument data. After data about the instrument is taken, the instrument is conveyed into the catch release mechanism and from there into is sent into the looped instrument chute. The instrument is received from the instrument chute at a packaging turret.

The packaging turret has a plurality of pouches ready to receive instruments. The turret receives the instrument into a pouch selected by the sterilization system. In a first embodiment, the pouches are different sizes and the sterilization system selects a pouch of an appropriate size for the instrument. In an alternative embodiment, the looped instrument chute is positioned over a selected pouch. In a further alternative embodiment, the turret moves under the instrument chute and the sterilization system directs the turret to position an appropriate pouch for the instrument under the chute.

The pouch with an instrument is then processed by the system as described above with regard to FIG. 1. The label printer prints labels. The pouches are labeled and processed in a sterilization unit and then placed into storage.

The automated system described above enables instruments to be identified, packaged and sterilized without human handling. The automated system provides the benefits of increased safety in the contaminated instruments are not handled by people who could become infected and also that the instruments themselves will not become contaminated from handling by people. Further, the system enables accurate sorting and labeling and efficient packaging.

It is to be understood that the above-identified embodiments are simply illustrative of the principles of the invention. Various and other modifications and changes may be made by those skilled in the art which will embody the principles of the invention and fall within the spirit and scope thereof.

We claim:

1. A system for packaging instruments for sterilization, comprising:
   an input for receiving instrument identification data;
   an instrument processor coupled to the input, the instrument processor including a database and an instrument analyzer, wherein
      the database is configured to store instrument type data, instrument packaging data, and package labeling data;
      the instrument analyzer is configured to identify an instrument based on the received instrument identification data to determine an instrument packaging type based on the identified instrument, and to determine a labeling associated with the identified instrument using data stored in the database; wherein
      the instrument analyzer is further configured to determine instrument handling instructions, packaging instructions, and labeling instructions based on the determined instrument packaging type; and
   an output coupled to the instrument processor, wherein the output is configured for sending the handling instructions, packaging instructions, and labeling instructions to at least one external device, the at least one external device including a packager configured to, for each identified instrument, automatically customize a variably sized package cut from bulk packaging material based on the received instrument identification data for the identified instrument, in response to packaging instructions received from the instrument processor, such that a plurality of variably sized packages are automatically produced.

2. The system of claim 1 wherein the at least one external device further comprises a labeler.

3. The system of claim 1 wherein the packager is a packaging turret holding a plurality of instrument pouches.

4. The system of claim 1, wherein the packager is a unit that holds a roll of packaging tubing and cuts and forms the customized packages.

5. The system of claim 1 wherein the at least one external device further comprises a transfer device for transferring the instrument from an instrument identification platform to a package element.

6. The system of claim 5 wherein the transfer device further comprises a catch and release mechanism.

7. The system of claim 5 wherein the transfer device further comprises a robotic arm.

8. The system of claim 5 wherein the package element is a peel pouch.

9. The system of claim 1 where the instrument analyzer is a machine vision sensor.

10. The system for packaging instruments of claim 1, wherein the instrument analyzer is further configured to determine whether the received instrument data is complete, and wherein, if the received instrument identification data is determined to be incomplete, comparing the incomplete instrument identification data to at least a portion of the stored instrument type data.

11. The system for packaging instruments of claim 10, wherein the instrument and corresponding packaging are further configured to be contemporaneously sterilizeable.

12. A method for packaging instruments for sterilization, the method comprising steps of:
   receiving at an input information relating to instrument identification data;
   identifying an instrument using the received instrument identification data and stored instrument data;
   determining and selecting an instrument packaging based on the received instrument identification data, the received instrument identification data including instrument size data associated with the identified instrument;
   determining label information for the packaging; and
   creating packaging instructions and labelling instructions to prepare the instrument and packaging based on the determined and selected instrument packaging, the instructions being configured to be provided to at least one packaging device configured to, for each identified instrument, automatically customize a variably sized package cut from bulk packaging material based on the received instrument identification data for the identified instrument, in response to packaging instructions received, such that a plurality of variably sized packages are automatically produced.

13. The method of claim 12 wherein the step of identifying the instrument further comprises reading an instrument label.

14. The method of claim 12 wherein the step of identifying the instrument further comprises comparing the information relating to the instrument with the stored instrument data.

15. The method of claim 14, wherein the step of receiving at the input information relating to the instrument identification data further comprises using machine vision.

16. The method of claim 12 wherein selecting instrument packaging further comprises selecting instrument packaging in response to an instrument identification.

17. The method of claim 12 further comprising sending the packaging instructions to a labeler.

18. The method of claim 12, wherein the at least one packaging device is a packaging turret.

19. The method of claim 12, wherein the at least one packaging device retains a roll of packaging tubing and cuts and forms the customized packages.

20. The method of claim 12 further comprising transmitting the packaging instructions to an instrument transfer device.

21. The method of claim 20 wherein the instrument transfer device is a catch and release mechanism.

22. The method of claim 20 wherein the instrument transfer device is a robotic arm.

23. The method of claim 12, the method further comprising contemporaneously sterilizing the instrument and corresponding packaging.

* * * * *